(12) United States Patent
Auger

(10) Patent No.: US 7,591,371 B2
(45) Date of Patent: Sep. 22, 2009

(54) ADHESIVE BANDAGE ENVELOPE

(76) Inventor: Raymond N. Auger, 709 Spruce St., Aspen, CO (US) 81611

(*) Notice: Subject to any disclaimer, the term of this patent is extended or adjusted under 35 U.S.C. 154(b) by 110 days.

(21) Appl. No.: 11/767,081

(22) Filed: Jun. 22, 2007

(65) Prior Publication Data

US 2008/0156687 A1 Jul. 3, 2008

Related U.S. Application Data

(62) Division of application No. 11/331,690, filed on Jan. 13, 2006, now abandoned.

(60) Provisional application No. 60/646,959, filed on Jan. 24, 2005.

(51) Int. Cl.
*A61F 13/00* (2006.01)

(52) U.S. Cl. .......................... 206/441; 221/58; 602/57

(58) Field of Classification Search ................ 206/440, 206/441, 820, 460; 221/33, 35, 45, 52, 56, 221/58, 59; 602/41, 43, 54–59
See application file for complete search history.

(56) References Cited

U.S. PATENT DOCUMENTS

| | | | | |
|---|---|---|---|---|
| 2,924,331 A | * | 2/1960 | Hoey | 206/441 |
| 2,965,223 A | * | 12/1960 | Schladermundt et al. | 206/441 |
| 2,969,145 A | * | 1/1961 | Hannauer, Jr. | 206/441 |
| 4,194,624 A | * | 3/1980 | Spiegelberg | 206/441 |
| 4,997,092 A | | 3/1991 | Dupont | |
| 5,133,477 A | | 7/1992 | Etheredge, III et al. | |
| 5,333,753 A | * | 8/1994 | Etheredge | 221/33 |
| 5,363,985 A | * | 11/1994 | Cornell | 221/46 |
| 5,643,188 A | | 7/1997 | Oliveira | |
| 6,213,343 B1 | | 4/2001 | Damikolas | |
| 6,648,172 B2 | * | 11/2003 | Leighton et al. | 221/35 |
| 6,719,137 B2 | | 4/2004 | Dotta | |
| 6,923,320 B2 | * | 8/2005 | Grossman | 206/440 |
| 7,445,142 B2 | * | 11/2008 | Salani et al. | 206/441 |

* cited by examiner

*Primary Examiner*—Luan K Bui
(74) *Attorney, Agent, or Firm*—Dorsey & Whitney LLP

(57) ABSTRACT

The present invention incorporates ways to rapidly open an envelope in which an adhesive bandage is packaged in a sterile manner. Such bandages are commonly described as Band Aids™. The method consists of a modification of the tabs currently used on one end of nearly all such envelopes. The modification consists of the enlargement of the tabs and the use of an additional fold to make the tabs easily gripped because they project out from the envelope. An additional embodiment of the invention causes all the envelopes in a box to be anchored in the box by tabs which are extensions of one half of each envelope, so that by pulling on the tab of the other half of the envelope, the bandage is both pulled from the box and extended from the envelope. An additional enhancement of the invention has one of the release strips protecting the adhesive portions of the bandage to adhere to the envelope, making the bandage ready for application without the need to remove that release strip through a separate action. A variety of bandage sizes may be included in one box, each size being available by a separate opening.

3 Claims, 5 Drawing Sheets

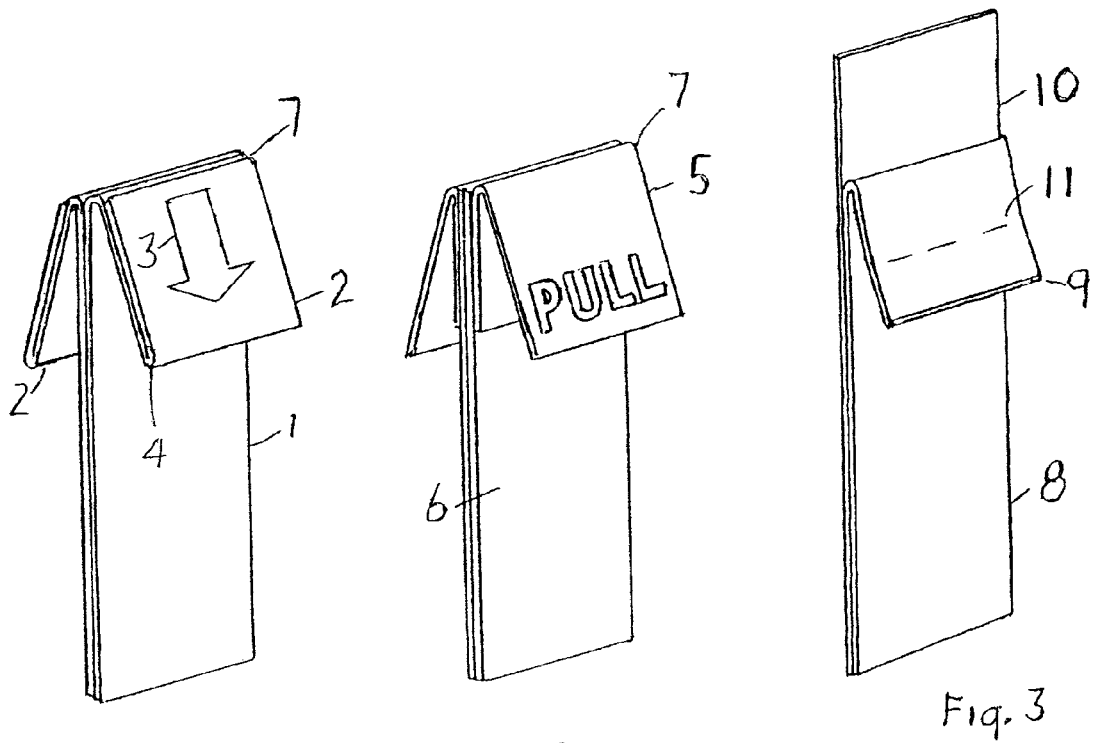
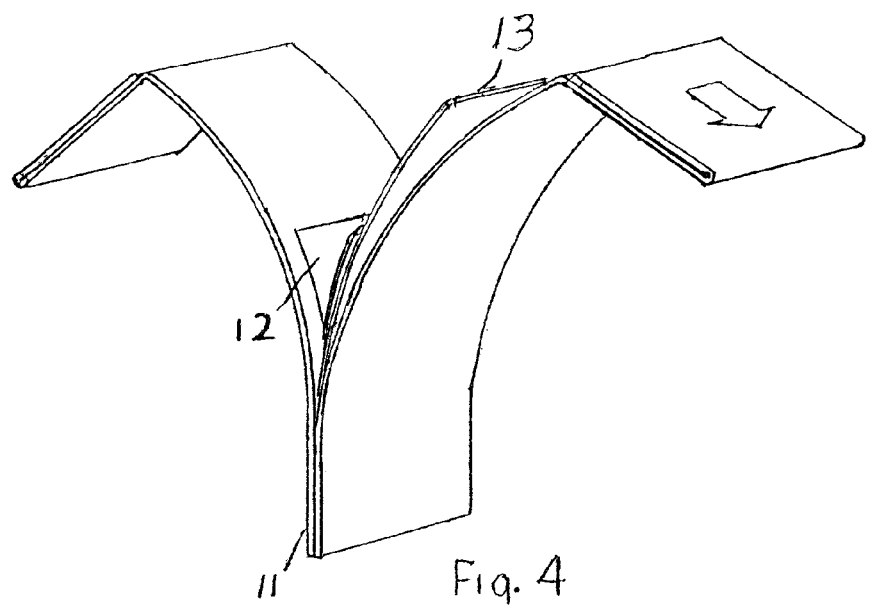

ADHESIVE BANDAGE ENVELOPE

CROSS-REFERENCE TO RELATED APPLICATION

The present application is a divisional of U.S. application Ser. No. 11/331,690, filed on Jan. 13, 2006 entitled "Adhesive Bandage Envelope," now abandoned, which claims the benefit under 35 U.S.C. § 119(e) of U.S. Provisional Application No. 60/646,959 filed on Jan. 24, 2005, which are hereby incorporated herein by reference in their entireties.

BACKGROUND OF THE INVENTION

1. Field of the Invention

The invention described herein relates to adhesive bandage packaging, and ways to improve them, in particular with regard to the ease and speed with which they can be used.

2. Prior Art

There are a number of patents which describe ways in which adhesive bandages of the Band-Aid variety (a trademark of Johnson and Johnson) are more rapidly and easily used. Oliveira in U.S. Pat. No. 5,643,188 shows a bandage attached to a release liner in a way which makes it easier to grip. Dupont in U.S. Pat. No. 4,997,092 shows a bandage envelope which can be pulled apart. Damikolas in U.S. Pat. No. 6,213,343 B1 shows a dispenser which strips away the envelope which encloses the bandages. Dotta in U.S. Pat. No. 6,719,137 shows a configuration for the bandage envelope which involves pulling on opposite ends of the envelope to release the bandage. Etheredge in U.S. Pat. No. 5,133,477 shows a plastic case with a cavity in place of the paper envelope used by currently available adhesive bandages, with only one release paper with its end folded over to permit easy removal. Grossman in U.S. Pat. No. 6,923,320 also shows various ways to release a bandage from its envelope by pulling on the opposite ends of the envelope. Grossman's patent includes a number of prior art references not cited above. Despite these and other packaging proposals, the half-dozen or so makers of bandages in envelopes vary little in their packaging structures. Nonetheless, consumer annoyance with the difficulties of using "Band Aids"™ is commonplace and near-universal.

The envelopes which encloses adhesive bandages being manufactured today typically have narrow "tabs", which range from ⅛th inch to ¼ inch wide, on one end of the envelope. In most cases these tabs are formed by folding a narrow strip on the ends of one or both of the adhesive-coated sides of the envelope on itself, so that if these tabs are manually gripped, the two halves of the envelope may be peeled apart. In practice, these narrow tabs can be gripped only by fingertips, and in the case of some bandage brands, they are difficult to separate, even though they are not glued together. In the case of some manufacturers, the tab on one half of the envelope protrudes beyond the other to some extent, up to ⅛th inch. Other makers give the tabs no significant separation at the ends of the envelope, so that peeling the envelope open is extremely difficult. In a few cases, there are no tabs, requiring that the envelope be torn open. Once opened, the envelope's bandage has its two adhesive halves covered by release strips, which, once pulled off, reveal the adhesive of the bandage. If a user pulls off both release strips at once, however, the adhesive is now attached to the fingers of the user, and hence loses some of its adhesive grip. Consequently, the ideal use of the bandage requires that only one release strip is removed at a time, with the exposed adhesive then placed on the skin while the bandage is held using the other release strip.

An alternative proper use is to pull both release strips partially off the adhesive, with the partially exposed adhesive then pressed to the skin while the remainder of the release strips are removed. However, in many cases, both release strips are removed at once, as previously described, with the possibility of the adhesive strips touching each other, or being folded on themselves, or at least sticking to the fingers of the user.

While the enlargement of envelope end tabs would be useful to help peel the envelope open, if they even lightly stick together, separating them can be difficult and time consuming. Often, the envelope must be opened rapidly, as a cut may be dripping blood. Or, the user may have poor eyesight or may have impaired manual dexterity, making it difficult to either find the tabs to separate and pull or to tear the envelope apart. In a few examples, the end of the envelope with the tabs is indicated by a color stripe. In other cases, there are no markings that would be useful to someone with poor eyesight or in a rush. Some makers of packaged bandages even pack them as pairs, side by side, or in groups, so that to open only one envelope, the packages must first be separated, and then one peeled, or torn, open. There are examples of envelopes which have no method of opening the envelope other than tearing off an end, a method which may result in the bandage being torn in the process.

Goals and Objectives of the Invention

The goal of the present invention is to speed the use of packaged adhesive bandages and to minimize mistakes in their application, such as the user touching the adhesive prior to it being applied to the area of the wound. The present invention provides a structure which enables the user with poor eyesight or trembling fingers to easily and rapidly peel open an adhesive bandage envelope, and to remove the bandage in a way which minimizes inadvertent finger contact with an adhesive surface prior to application.

For the average user, the time required by contemporary designs from box to skin varies from 22 to 35 seconds, sometimes longer, even over a minute, depending on whether the envelope tabs easily separate or not and whether the person using the bandage knows how the tabs should be separated. If the envelope is torn open rather than peeled apart, total time is often over 40 seconds, possibly longer if the adhesive bands stick to the fingers of the user. Some adhesive bandage envelope designs provide little or no clue to which end should be opened, and are so difficult to peel apart that they invite the envelopes to be torn open, the slowest way to remove the bandage. Using the structure described herein, however, total time can be as low as 10 seconds or less, with a typical high of 15 seconds. The most important aspects of the present invention are that the bandages employing its teachings can be rapidly used by individuals with poor eyesight and trembling hands, and that there is only modest added manufacturing cost associated with its use. An advantage of a major embodiment of the invention is that it allows an adhesive bandage to be extracted from its box by pulling on a tab extending from the box which also peels the envelope apart as the bandage is removed. Another advantage of the invention is that it allows one box to contain various sizes and types of bandages, each with their own exit door, so that a user need not randomly pull bandages from a box looking for a particular size.

BRIEF DESCRIPTION OF THE INVENTION

The present invention incorporates ways to rapidly open an envelope in which an adhesive bandage is packaged in a sterile manner. The method consists of a modification of the tabs currently used on one of the ends of nearly all such envelopes. My modification consists of the enlargement of the tabs and the use of an additional fold to make the tabs easily gripped because they project out from the envelope. An additional embodiment of the invention causes all the envelopes in a box to be anchored in the box by tabs which are extensions of one half of each envelope, so that by pulling on the tab of the other half of the envelope, the bandage is both pulled from the box and extended from the envelope. An additional enhancement of the invention has one of the release strips protecting the adhesive portions of the bandage to adhere to the envelope, making the bandage ready for application without the need to remove that release strip through a separate action.

BRIEF DESCRIPTION OF THE DRAWINGS

FIG. 1 is a perspective view of a bandage envelope with two folded tabs.

FIG. 2 is a perspective view of a bandage envelope with attached tabs.

FIG. 3 is a perspective view of a bandage envelope with only one tab folded.

FIG. 4 is a perspective view of the envelope assembly in FIG. 1 when opened.

DETAILED DESCRIPTION OF PREFERRED EMBODIMENTS

Figure 5:
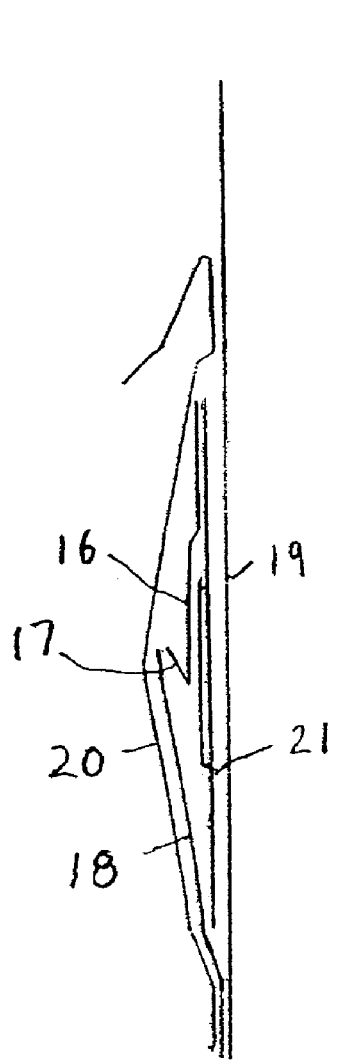
FIG. 5 is a schematic view of the envelope assembly shown in FIG. 3.

The present invention consists, in part, of at least one folded tab on the end of a bandage envelope, as seen in FIG. 1. The tab itself may or may not be made by folding the adhesive surfaces of the tab on itself as seen in FIG. 1, or unfolded, as in FIG. 2. The fact that at least one tab is folded away from the bond or fold line of the bandage envelope insures that they will not stick together, a major problem with bandage envelopes as currently manufactured. Because the tabs are folded, they are deflected outward from the envelope making their function more obvious. These tabs are of a size easily seen and gripped by the user. One tab may be held by the teeth while the other is pulled by a free hand, partially opening the envelope. The tabs may be enlargements of the existing type of tab, with one or both folded outward away from the other tab, or they may be separate strips of paper stuck to the envelope as seen in FIG. 2. A second feature of the invention which may be optionally used, attaches one of the release strips to one side of the envelope, so that when the envelope is opened and the bandage is removed, one of its adhesive bands is already exposed and ready for use. After that half of the bandage is attached to the skin of the user, the second release strip can be removed to complete the adhesion of the bandage to skin. Although the removal of a release strip may take only two or three seconds, there are situations where the user may be dripping blood profusely from a deep finger cut, and those seconds are important in terms of what the blood drips onto. Also, if only one release strip has been removed, the bandage can be applied with one hand. If both release strips are removed before the bandage is applied, applying the bandage generally requires two hands.

From the perspective of manufacture, there are two alternative methods of obtaining the invention's tab structure. The first might be viewed as a retrofit solution: separate peeling tabs can be added to packaged adhesive bandages as currently manufactured. Bandages already made and in inventory can be so modified. This solution has the advantage of imposing no changes in the design of the envelope or its production machinery. The second solution imposes a design change on machinery used to currently make the bandage's envelopes. The tabs are currently made by some manufacturers by folding approximately one eighth of an inch of the inner adhesive-covered envelope paper on itself, although Johnson and Johnson eliminates the adhesive from the tab area. To obtain the performance of the present invention, these tabs would be one half inch to three quarters of an inch in size, and then at least one of them folded back against the envelope. This second fold separates the tabs and makes their function obvious even for someone who has never seen such a structure. Because the tabs do not face each other, they need not be folded on themselves to cover their adhesive surfaces, as is the case with the tabs used by many current manufactures of envelopes.

A preferred embodiment of the invention causes one tab to be substantially longer than the other. This tab is lengthened sufficiently to permit it to be used to secure a group of the bandage envelopes to each other, and then to the bottom or top flap of a box from which they can be pulled by the free tab, opening the envelopes as they are pulled from their box.

FIG. 1 shows an envelope 1 of the type which contains an adhesive bandage, with folded tabs 2 used to pull the halves of the envelope apart. Typical of bandage envelopes currently in use, the insides of the envelope are coated with an adhesive, so that pressing them together completes the sealed space into which the adhesive bandage is placed. Printed on tabs 2 may be indicators of the action required to open the envelope, for example, an arrow 3, or shown in FIG. 2, a word such as pull, or any combination of the two. Tabs 2 in FIG. 1 are made by folding the paper of which the envelope is made on itself, with the adhesive surfaces in contact, at fold 4, whereas the tabs 5 in FIG. 2 are made by adhering separate structures 5 onto the body of the envelope 6. The use of separate structures 5 has the advantage of being able to use a material which causes the fold 7 to have a spring characteristic which causes tab 5 to stand out from envelope 6. Desirably the tabs form an angle in the range of 15 to 179 degrees with the remainder of the bandage envelope. If tab 5 is gripped by teeth, for example, having it clearly separated from envelope 8 is most desirable. Since the tabs 2 and 5 will be compressed against the envelopes when the bandages are boxed, having elasticity in folds 7, is a nice feature of the invention. The fold 7 in FIG. 1 may be obtained by a method which bends tabs 2 only enough to permit the insertion of the bandages into a box so that when removed from the box, the tabs spring open to an easily-seen angle from the envelope.

FIG. 3 shows an envelope 8 with but one folded tab 9, the other tab 10 being straight. Tab 9 has an optional second fold at 11 intended to deflect tab 9 away from bandage envelope 8 so as to make it more easily gripped by the user. Since the outward facing surfaces of tabs 10 and 11 are coated with adhesive, there is some potential for them to stick to an adjacent envelope in its package. This possibility is diminished by the type of adhesive used, and whether it primarily bonds with itself, and by minimizing pressure between envelopes in a package. It is also possible to coat the outside of the envelopes which face the adhesive tabs with a releasing agent.

FIG. 4 shows an envelope of the type seen in FIG. 1 in the process of being peeled open by its tabs 15. The release strip 12 covering the lower half of the bandage 13 is shown attached to envelope half 14. In theory, this could be accomplished by coating one side of release strip 12 with an adhesive.

FIG. 5 is a schematic side view of a bandage assembly such as shown in FIG. 3. The two halves of the envelope are 19 and 20. Two release strips are shown, 16 and 18. Strip 16 has its end 17 folded so that its release-coated surface faces release strip 18. Release strip 18 will adhere to the envelope half 20 when the envelope is peeled apart because of the fact that the release surfaces of strip 16 and 18 face each other at 17, providing virtually no adhesion, whereas strip 18 is lightly bonded to envelope half 20. The bond between envelopes halves 19 and 20 is weak, since it permits the envelope halves to be easily peeled apart. Typically, the bond between 18 and the adhesive of bandage 21 (even though 18 has a release-coated surface) is greater than the bond between 18 and 20. Only if you peel 18 and 21 apart starting from the top end of 18, which is against the bandage gauze, and has no tack at all, does the adhesion between 18 and 20 predominate, and once the peel is started, that bond remains intact. However, in the case of 16 and 21, the peel starts at the top, where the contest is between the adhesive of the bandage 21 and release strip 16 versus the weak adhesive of 20. Even though release strip 16 has a release coat, it nonetheless sticks to the adhesive of bandage 21 to a greater degree than to the adhesive of the envelope 20. The little fold 17 is intended to make sure that the release strip 16 does not stick to the other release strip 18. Thus, when you pull the envelope open, the upper release strip 16 tends to stick to the bandage 21, while the lower release strip 18 tends to stick to the envelope 20.

Figure 6:
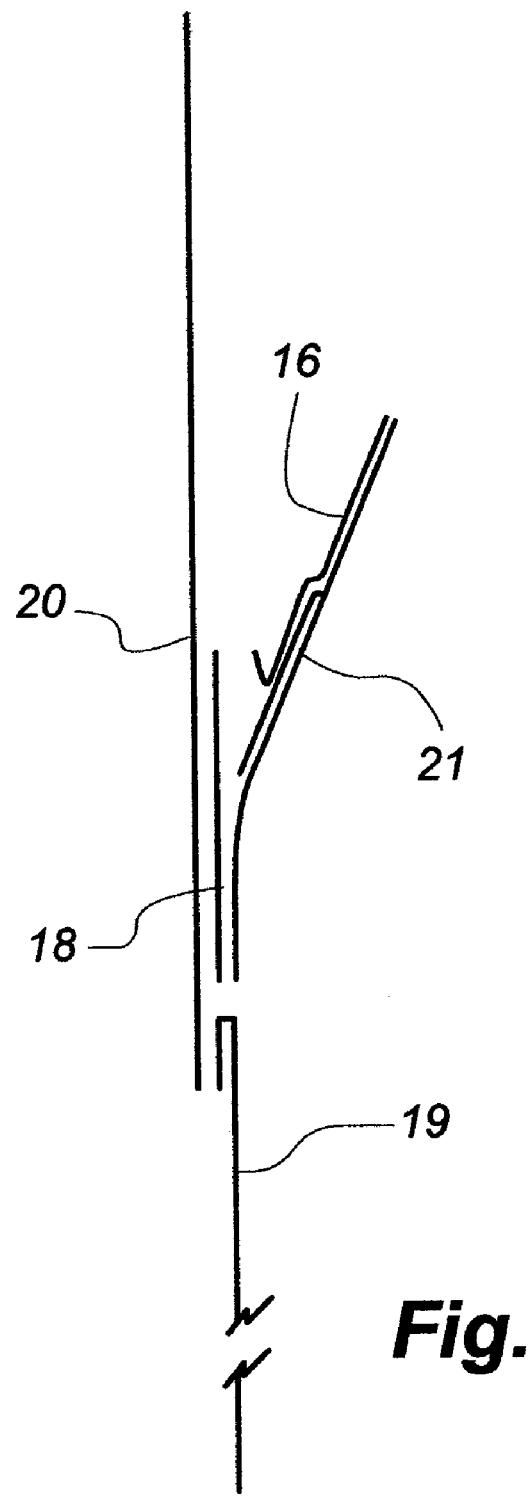
FIG. 6 is a schematic view of the envelope assembly in FIG. 5 when opened.

FIG. 6 shows the same configuration as in FIG. 5, with the envelope opened. Envelope side 19 is shown separated from and pulled down from side 20. The bandage 21 is clear of the envelope, easily pinched and lifted for removal and use, leaving release strip 18 on envelope half 20. It is desirable to enable the user to hold the bandage by the end having its adhesive covered, applying the uncovered end of the bandage to a specific section of skin. Envelope half 19 may be fully pulled free from envelope half 20, rather than partially attached as shown. Or, alternatively, envelope halves 19 and 20 may be one sheet of paper, folded to cover the bandage.

Figure 7:
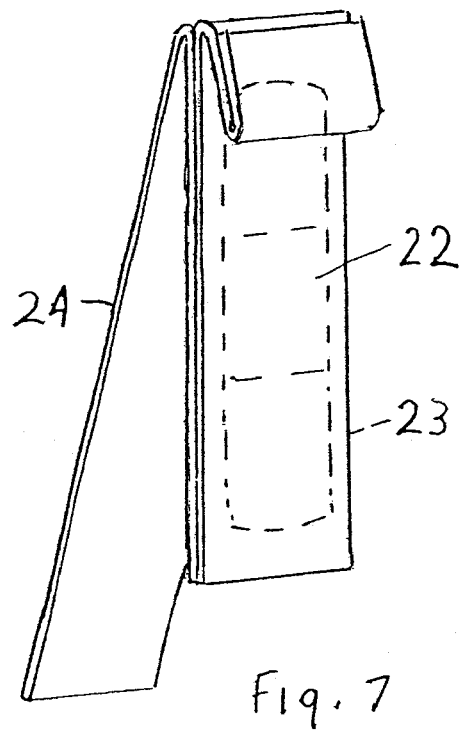
FIG. 7 is a perspective view of a modification of the envelope assembly in FIG. 1.
Figure 8:
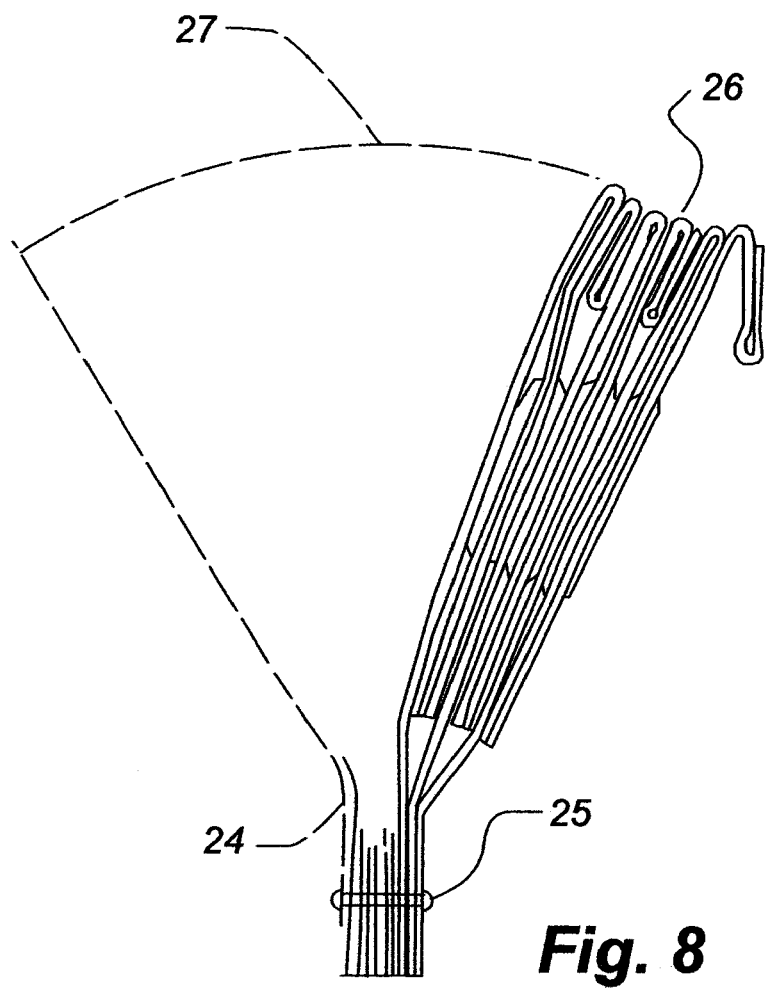
FIG. 8 is a side view of a group of envelope assemblies such as seen in FIG. 7.
Figure 9:
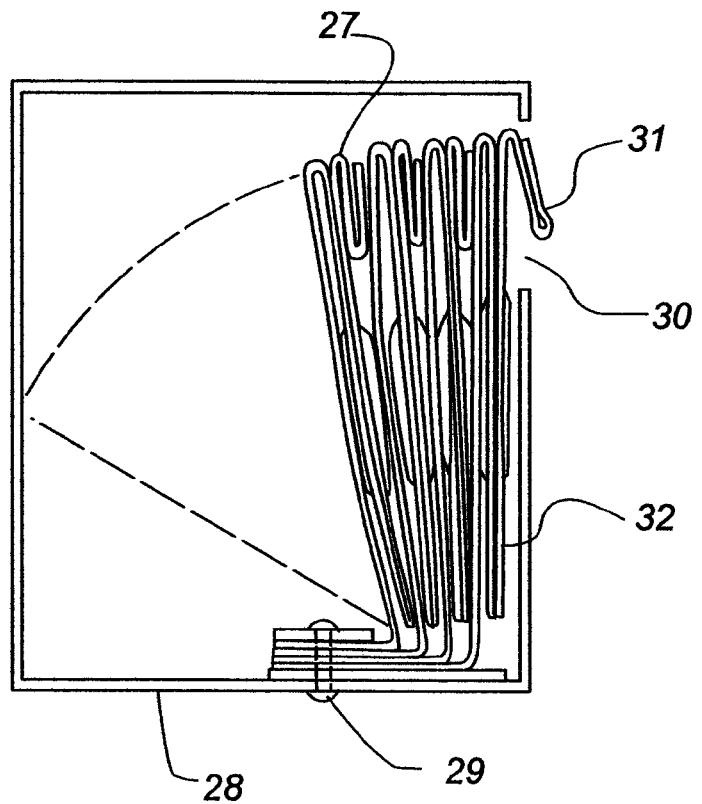
FIG. 9 is a section view of a box containing a group of envelope assemblies as seen in FIG. 8.
Figure 10:
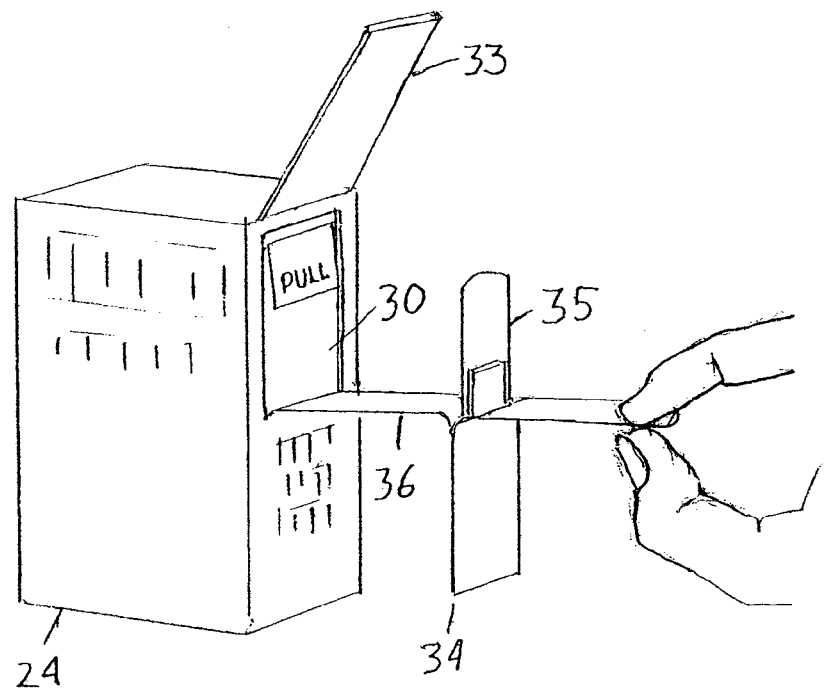
FIG. 10 is a perspective view of the assembly in FIG. 9 in operation.

FIG. 7 shows an adhesive bandage 22 by dashed lines in an envelope 23 having one of its halves 24 substantially longer than envelope 23. FIG. 8 shows how a number of extended tabs 24 can be stapled 25 or joined by other methods, such as adhesives or clips, into a pack or assembly 26 whose overall shape is shown by a dashed line 27. FIG. 9 shows the fan-like assembly 27 in FIG. 8 as it would appear inserted and stapled 29 into a box 28 shown in simplified form. Box 28 is shown with a door or port 30 through which the envelope tab 31 projects so that it can be pulled by a user. When tab 31 is pulled through window 30, envelope 32 is peeled apart, as seen in FIG. 10. Also shown in FIG. 10 is a flap 33 which covers window 30 prior to the box 24 being opened. Flap 33 may seal window 30 by an adhesive tape or the insertion of a tab, not shown, into box 24. FIG. 10 shows bandage 35 without the release paper that covers the adhesive tab of the bandage for illustrative clarity.

After envelope 34 in FIG. 10 is pulled apart sufficiently for the bandage 35 to be removed, the envelope half 36 which extends through window 30 must be torn out of box 24. This may be done by perforating envelope half 36 at any point within box 24, or by forming the bottom edge of window 30 into a saw-tooth shape to permit paper 36 to be torn at that point. A metal saw-like edge can also be attached along the bottom of window 30 to facilitate ripping paper tab 36 at that point. As the bandage envelopes in FIG. 10 are removed, it is desirable that the next envelope in the stack or fan move against window 30. This can be encouraged in a number of ways, one being shown in FIG. 11. In this figure a spring-like L shaped pressing element 41, made of cardboard or plastic, pushes the assembly of bandages, 37, towards window 40. Other materials may be used in place of element 41, for example, elastic foam.

Figure 11:
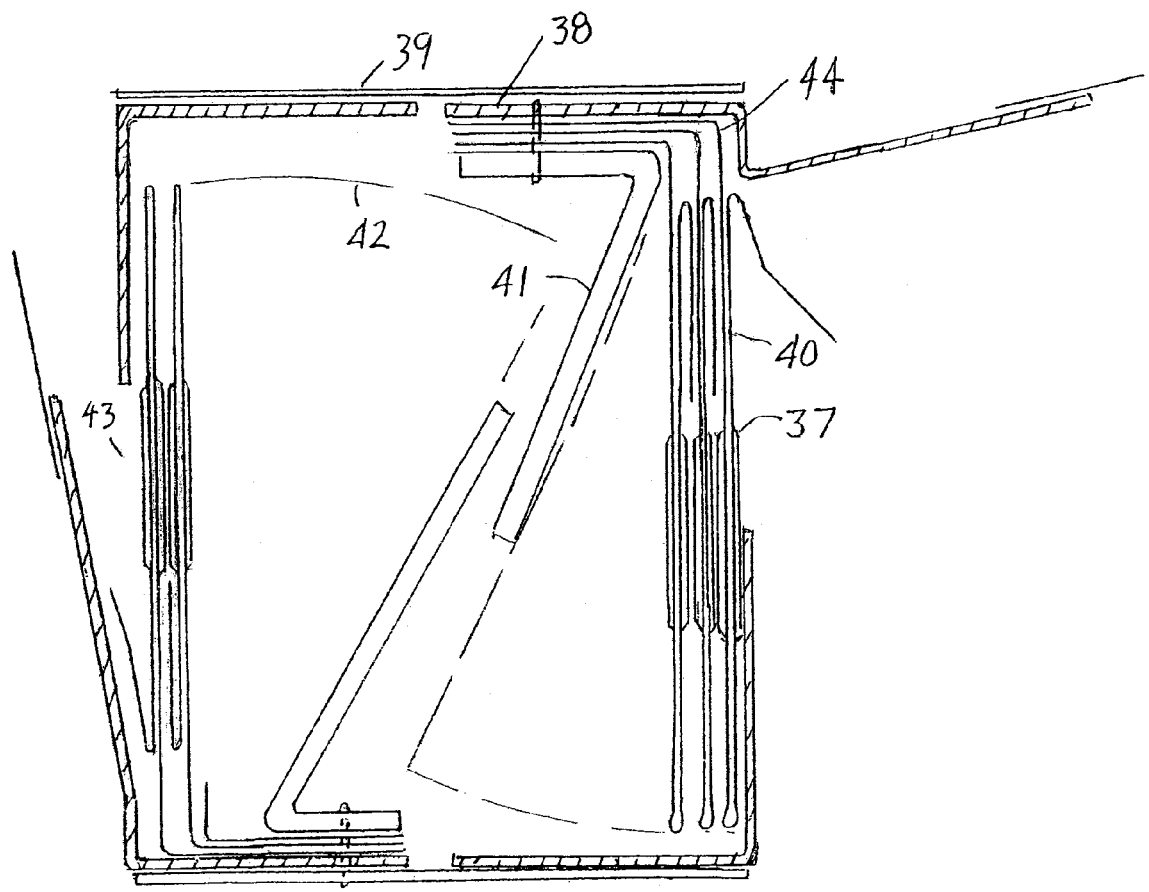
FIG. 11 is a section view of an assembly such as in FIG. 10, showing attachment to the top of the box rather than the bottom as in FIG. 9, and the use of two bundles of bandages in one box.

FIG. 11 shows three bandage envelopes 37 attached to one of the top flaps 38 of the box 39. The three envelopes are illustrative of a group which may include as many as forty or more envelopes. Bundled bandages 37 are pushed towards door opening 40 by deflector 41 which may be made of cardboard, plastic or anything with sufficient elasticity to provide some modest pressure on bandage assembly 37. A virtue of the configuration in FIG. 11 which uses upper box flap 38 as the bandage envelope mounting point, is that it minimizes the length of the tabs 44 needed to secure the group of bandage envelopes 37 to box 39 and thus forms an alternative to the embodiment of FIG. 9. Although somewhat schematically illustrated, the two halves of each envelope of the group 37 are shown as one piece of paper, folded at the bottom, rather than two pieces glued together at their bottoms. The virtue of this variation of the invention is that when a bandage is removed from an envelope, it remains as one piece of paper, and is easier to dispose of than two. The possibility of employing this variation of the invention has been previously mentioned with regard to schematic illustration FIG. 6. FIG. 11 also shows a second assembly of bandages, outlined by dashed line 42, which can fit in the same box as assembly 37, this second assembly to be removed through opening 43.

This second assembly of bandages could be a different size than assembly 37. Additional assemblies of bandages of various sizes may be added to the same box, each with its own access window.

An advantage of the present invention is that when a conventional (prior art) adhesive bandage envelope is removed from its envelope, the user must dispose of at least four bits of paper: each side of the envelope, and both of the release slips. If the envelope is torn open, there may be additional separate bits of paper. With the present invention, the user typically has two pieces of paper to dispose of, that being the partially opened envelope or, alternatively, the one-piece envelope, and one release paper, the other being attached to the envelope.

An important aspect of the design of any product which is an improvement or advancement of a pre-existing product is the extent to which the existing manufacturing equipment which is being used to make the product can be modified or converted to make the improved version of the product. In the case of the invention described herein, the dimensions of the envelope's halves and the addition of one fold, 6 in FIGS. 1 and 2, are the major product changes, but relatively minor in terms of production machine design. Box 39 in FIG. 11 requires more than a minor modification of the prior art boxes into which adhesive bandages are packed for sale, but the technology of box manufacture is well-known and old art. The machinery which assembles the bandages into the fan-shape of FIG. 9 and then insert that fan into box 28 may be the most complex new item needed to manufacture the present invention.

FIG. 11 shows that more than one group of bandages may be located in one box, each with its own window for removal. A significant advantage of box structures such as in FIG. 11 is that it allows each door to be identified on the outside of the box in terms of the type or size of bandage available through it. At present, boxes of packaged bandages which contain an assortment require that the user pick through them looking for the type or size required.

Another advantage of the method of releasing bandages provided by the present invention is that each bandage envelope may be numbered or given some other indication of the number in the box, so that, for example, if a box contains 20 bandages of a given type, when the 18th bandage is pulled, it can have printing on it which says "only two more left, time to buy more", or can simply be colored red as a warning.

Although the present invention has been described with a certain degree of particularity, it is understood the disclosure has been made by way of example, and changes in detail or structure may be made without departing from the spirit of the invention as defined in the appended claims.

The invention claimed is:

1. A combination of an adhesive bandage, a removable enclosure for the bandage and a box for containing a plurality of said enclosures comprising:

an adhesive bandage strip;

an enclosure for said strip having only two components which are releasably secured together in confronting relationship capturing the strip therebetween, one of said confronting components having a short tab at one end and the other component having a relatively long tab, and a box for containing a plurality of said enclosures, said box having a window in which said short tab of an enclosure is exposed, said long tab of said enclosure being secured to said box, whereby pulling on said short tab while said long tab remains secured to said box removes said strip from said box and said enclosure.

2. The combination of claim 1 further including a resilient piece of material in said box biasing said enclosure toward said window.

3. The combination of claim 1 wherein said box has a second window and wherein there are two groups of said enclosures in said box, one group of said enclosures having the short tabs of its enclosures aligned with said first-mentioned window and said second group of enclosures having the short tabs of its enclosures aligned with said second window.

* * * * *